United States Patent
Matsuo et al.

(10) Patent No.: US 11,895,762 B2
(45) Date of Patent: Feb. 6, 2024

(54) HOLDING MEMBER, IRRADIATOR, AND PLASMA APPARATUS

(71) Applicant: SEKISUI CHEMICAL CO., LTD., Osaka-fu (JP)

(72) Inventors: Tatsuya Matsuo, Kyoto (JP); Yoshishige Takikawa, Kyoto (JP); Yu Nagahara, Kyoto (JP); Naomichi Saito, Kyoto (JP); Masaki Iwasaki, Kyoto (JP); Takaya Oshita, Ibaraki (JP)

(73) Assignee: SEKISUI CHEMICAL CO., LTD., Osaka (JP)

( * ) Notice: Subject to any disclaimer, the term of this patent is extended or adjusted under 35 U.S.C. 154(b) by 0 days.

(21) Appl. No.: 17/909,910

(22) PCT Filed: Mar. 17, 2021

(86) PCT No.: PCT/JP2021/010776
§ 371 (c)(1),
(2) Date: Sep. 7, 2022

(87) PCT Pub. No.: WO2021/187513
PCT Pub. Date: Sep. 23, 2021

(65) Prior Publication Data
US 2023/0105530 A1     Apr. 6, 2023

(30) Foreign Application Priority Data
Mar. 18, 2020    (JP) ................... 2020-047986

(51) Int. Cl.
*H05H 1/24*     (2006.01)
*A61L 2/00*     (2006.01)
(Continued)

(52) U.S. Cl.
CPC .......... *H05H 1/2443* (2021.05); *A61L 2/0011* (2013.01); *A61L 2/26* (2013.01);
(Continued)

(58) Field of Classification Search
CPC .. H05H 1/2443; H05H 1/2431; A61L 2/0011; A61L 2/26; A61L 2202/11; A61N 1/44
See application file for complete search history.

(56) References Cited

U.S. PATENT DOCUMENTS

2017/0339776 A1* 11/2017 Knoll .................... A61L 2/0011

FOREIGN PATENT DOCUMENTS

| JP | 11-285832 | 10/1999 |
|---|---|---|
| JP | 11285832 A * | 10/1999 |

(Continued)

OTHER PUBLICATIONS

International Search Report dated Jun. 1, 2021 in corresponding International Application No. PCT/JP2021/010776.
(Continued)

*Primary Examiner* — Mary Ellen Bowman
(74) *Attorney, Agent, or Firm* — Wenderoth, Lind & Ponack, L.L.P.

(57) ABSTRACT

An irradiator includes: a first electrode to which a voltage is applied for generating a plasma; and a holding member holding the first electrode; wherein: the holding member has a first member and a second member that are in contact with each other to constitute an accommodation space accommodating the first electrode; and a contact surface between the first member and the second member includes a non-perpendicular contact surface that is non-perpendicular to an axis of the first electrode.

11 Claims, 9 Drawing Sheets

(51) Int. Cl.
*A61L 2/26* (2006.01)
*A61N 1/44* (2006.01)
(52) U.S. Cl.
CPC ........ H05H 1/2431 (2021.05); *A61L 2202/11* (2013.01); *A61N 1/44* (2013.01)

(56) References Cited

FOREIGN PATENT DOCUMENTS

| JP | 2017-35281 | | 2/2017 | | |
|----|------------|---|--------|---|---|
| JP | 2017035281 | A * | 2/2017 | | |
| WO | WO-2016071680 | A1 * | 5/2016 | ........... | A61B 18/042 |

OTHER PUBLICATIONS

International Preliminary Report on Patentability dated Sep. 20, 2022 in corresponding International Application No. PCT/JP2021/010776.

* cited by examiner

HOLDING MEMBER, IRRADIATOR, AND PLASMA APPARATUS

TECHNICAL FIELD

The present invention relates to a holding member, an irradiator, and a plasma apparatus.

BACKGROUND ART

A technique of utilizing a plasma for dental therapy, etc. has been proposed (see JP 2017-35281 A). A hand piece for plasma irradiation is disclosed in JP 2017-035281 A applies a plasma from its tip to an affected area to sterilize it. The hand piece for plasma irradiation of JP 2017-035281 A comprises: a second electrode (33) electrically connected to an electric connector (40), an insulation tube (36) covering the electrode for electrical insulation, and a housing accommodating the electrode and the insulation tube. The insulation tube (36) has a cylindrical shape to cover a root part of the second electrode (33). One end of the insulation tube (36) is attached to the electric connector (40). A member such as a glass support member (38) is attached to the other end of the insulation tube (36).

DISCLOSURE OF THE INVENTION

When assembling an assembly by attaching one end of an insulation tube to an electrode and by attaching another member to the other end of the insulation tube, there is a room for improvement in the ease of assembly. In order to improve the ease of assembly of an irradiator for plasma irradiation, it seems preferable that a holding member holding the electrode has a dividable structure. However, as described below, when the holding member has a dividable structure to improve the ease of assembly, there is concern that a short circuit occurs between the electrode and an object outside the holding member.

The object of the present invention is to provide a holding member, an electrode holder, an irradiator, and a plasma apparatus which are capable of effectively solving such a problem.

An irradiator according to the present invention comprises: a first electrode to which a voltage is applied for generating a plasma; and a holding member holding the first electrode; wherein: the holding member has a first member and a second member that are in contact with each other to constitute an accommodation space accommodating the first electrode; and a contact surface between the first member and the second member includes a non-perpendicular contact surface that is non-perpendicular to an axis of the first electrode.

In the irradiator according to the present invention, any perpendiculars toward the axis through the non-perpendicular contact surface may be non-parallel to the non-perpendicular contact surface.

In the irradiator according to the present invention, the non-perpendicular contact surface may define an angle that is larger than 45° with respect to a radial direction perpendicular to the axis.

In the irradiator according to the present invention, the non-perpendicular contact surface may surround the first electrode from a circumference about the axis.

In the irradiator according to the present invention, the non-perpendicular contact surface may include a first non-perpendicular contact surface, and a second non-perpendicular contact surface that is apart from the first non-perpendicular contact surface in a radial direction perpendicular to the axis.

In the irradiator according to the present invention, the first electrode may have a terminal connected to an external power source; and the non-perpendicular contact surface may be located outside the terminal in a radial direction perpendicular to the axis.

In the irradiator according to the present invention, the contact surface may include a perpendicular contact surface perpendicular to the axis; and the perpendicular contact surface may be located in an area different from an area in which the terminal is located in a direction along which the axis extends.

In the irradiator according to the present invention, the first electrode may have a larger diameter part having a largest outward projection length in a radial direction perpendicular to the axis; and the non-perpendicular contact surface may be located outside the larger diameter part in the radial direction.

In the irradiator according to the present invention, the contact surface may include a perpendicular contact surface perpendicular to the axis; and the perpendicular contact surface may be located in an area different from an area in which the larger diameter part is located in a direction along which the axis extends.

In the irradiator according to the present invention, a second electrode may be attached to the holding member such that the second electrode is opposed to a part of the first electrode; and the non-perpendicular contact surface may be located in an area different from an area in which the second electrode is located in a direction along which the axis extends.

The irradiator according to the present invention may comprise an outer cylinder member that is electrically grounded and accommodates the first electrode entirely, wherein the non-perpendicular contact surface is located between the first electrode and the outer cylinder member.

A plasma apparatus according to the present invention comprises the aforementioned irradiator.

A holding member according to the present invention is a holding member for holding a first electrode to which a voltage is applied for generating a plasma, wherein: the holding member has a first member and a second member, and constitutes an accommodation space accommodating the first electrode by the first member and the second member in contact with each other; and a contact surface between the first member and the second member includes a non-perpendicular contact surface that is non-perpendicular to an axis of the first electrode.

The holding member, the irradiator, and the plasma apparatus of the present invention can improve the ease of assembly, while suppressing a short circuit between the electrode and an object outside the holding member.

MODE FOR CARRYING OUT THE INVENTION

Figure 1:
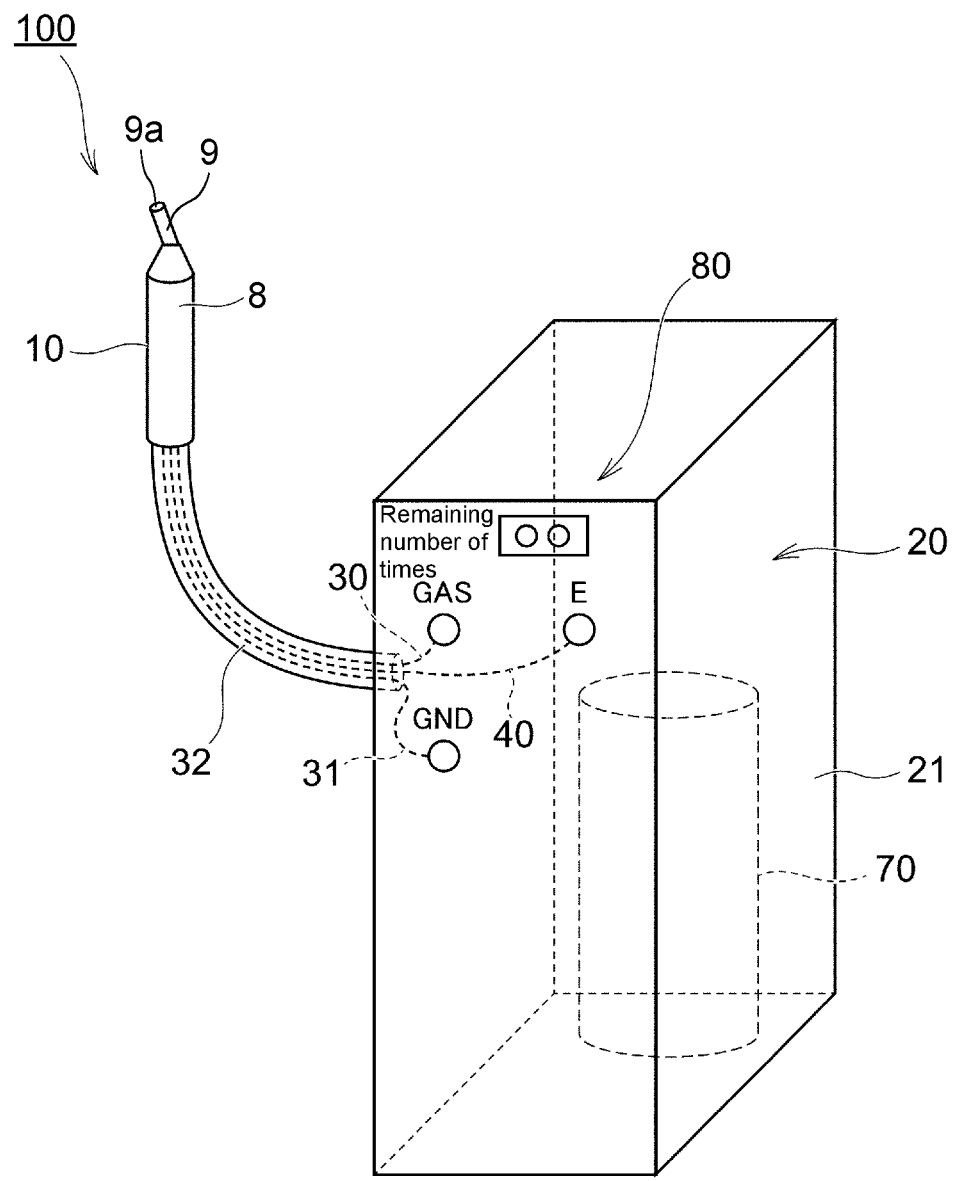
FIG. 1 is a schematic view showing a plasma apparatus according to an embodiment of the present invention.

An embodiment of the present invention will be described herebelow with reference to the drawings. In the drawings attached to the specification, a scale dimension, an aspect ratio and so on are changed and exaggerated from the actual ones, for the convenience of easiness in illustration and understanding.

An embodiment of the present invention will be described herebelow with reference to the drawings. In the drawings attached to the specification, a scale dimension, an aspect ratio and so on are changed and exaggerated from the actual ones, for the convenience of easiness in illustration and understanding.

Further, terms specifying shapes, geometric conditions and their degrees, e.g., "parallel", "perpendicular", "same", etc., and values of a length and an angle are not limited to their strict definitions, but construed to include a range capable of exerting a similar function, unless otherwise specified.

A plasma apparatus of the present invention is a plasma jet irradiation apparatus or an active gas irradiation apparatus. Both the plasma jet irradiation apparatus and the active gas irradiation apparatus generate a plasma. The plasma jet irradiation apparatus applies the generated plasma and an active species directly to an irradiation target. The active species is generated by reaction between a gas in the plasma or a gas around the plasma and the plasma. The active species is, for example, active oxygen species or active nitrogen species. The active oxygen species is, for example, hydroxyl radical, singlet oxygen, ozone, hydrogen peroxide, superoxide anion radical, etc. The active nitrogen species is, for example, nitrogen monoxide, nitrogen dioxide, peroxynitrite, dinitrogen trioxide, etc. The active gas irradiation apparatus applies an active gas containing an active species to an irradiation target. The active species is generated by reaction between a gas in the plasma or a gas around the plasma and the plasma.

Figure 2:
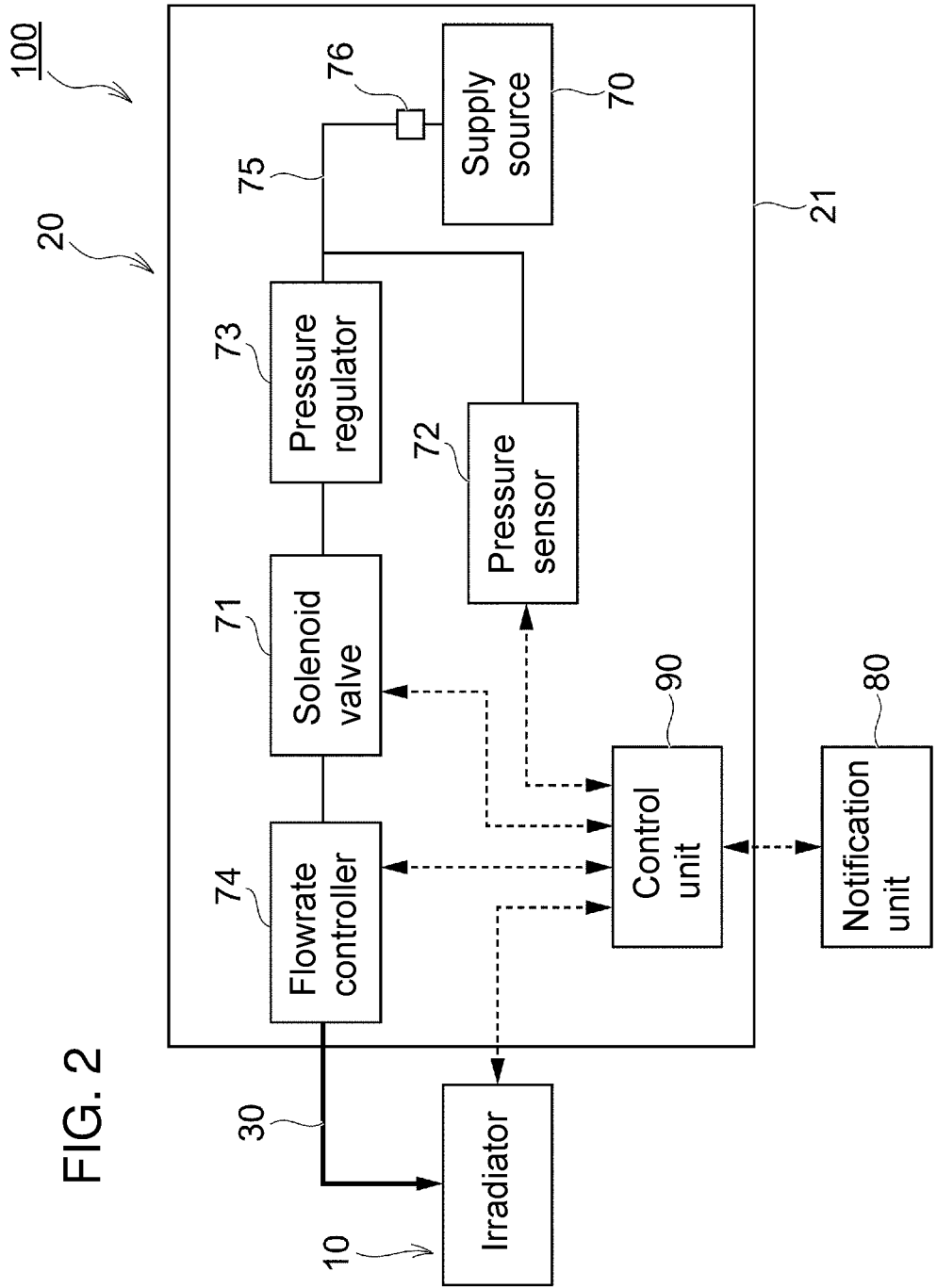
FIG. 2 is a block diagram showing a schematic structure of the plasma apparatus according to the embodiment of the present invention.

An embodiment of the plasma apparatus, the irradiator, and the holding member is described herebelow. The plasma apparatus in this embodiment is an active gas irradiation apparatus, for example. As shown in FIGS. 1 and 2, the active gas irradiation apparatus 100 in this embodiment comprises an irradiator 10, a supply unit 20, a gas pipeline 30, a voltage supply line 40, a supply source 70, a notification unit 80, and a control unit 90 (operation unit).

The irradiator 10 ejects an active gas generated in the irradiator 10. The irradiator 10 is operated by a doctor or the like, and has a shape, a size, and a weight that are easy to operate by human hands. The irradiator 10 is connected to the supply unit 20 through the gas pipeline 30, a ground wire 31, and the voltage supply line 40. In the example shown in FIG. 1, the irradiator 10 comprises an outer cylinder member 8 described later, and a nozzle 9 forming a distal end of the irradiator 10. The nozzle 9 is attached to a distal end of a holding member 1 described later. The nozzle 9 has therein a flow channel through which an active gas flows. The active-gas flow channel in the nozzle 9 is in communication with a flow channel through which a plasma generation gas flows in the holding member 1 described later. When the irradiator 10 has the nozzle 9, an active gas passes through an irradiation opening 1c1 of a third member 1c of the holding member 1 described later, and the flow channel in the nozzle 9 to be ejected from a nozzle irradiation opening 9a located on the distal end of the nozzle 9. The gas pipeline 30 and the voltage supply line 40 are accommodated in a single cable 32. The supply unit 20 supplies the irradiator 10 with power and a plasma generation gas. The supply unit 20 accommodates the supply source 70. The supply source 70 accommodates the plasma generation gas. The supply unit 20 is powered by a power source such as a 100-V household power supply. Alternatively, the supply unit 20 may incorporate a rechargeable battery as a power source.

Figure 3:
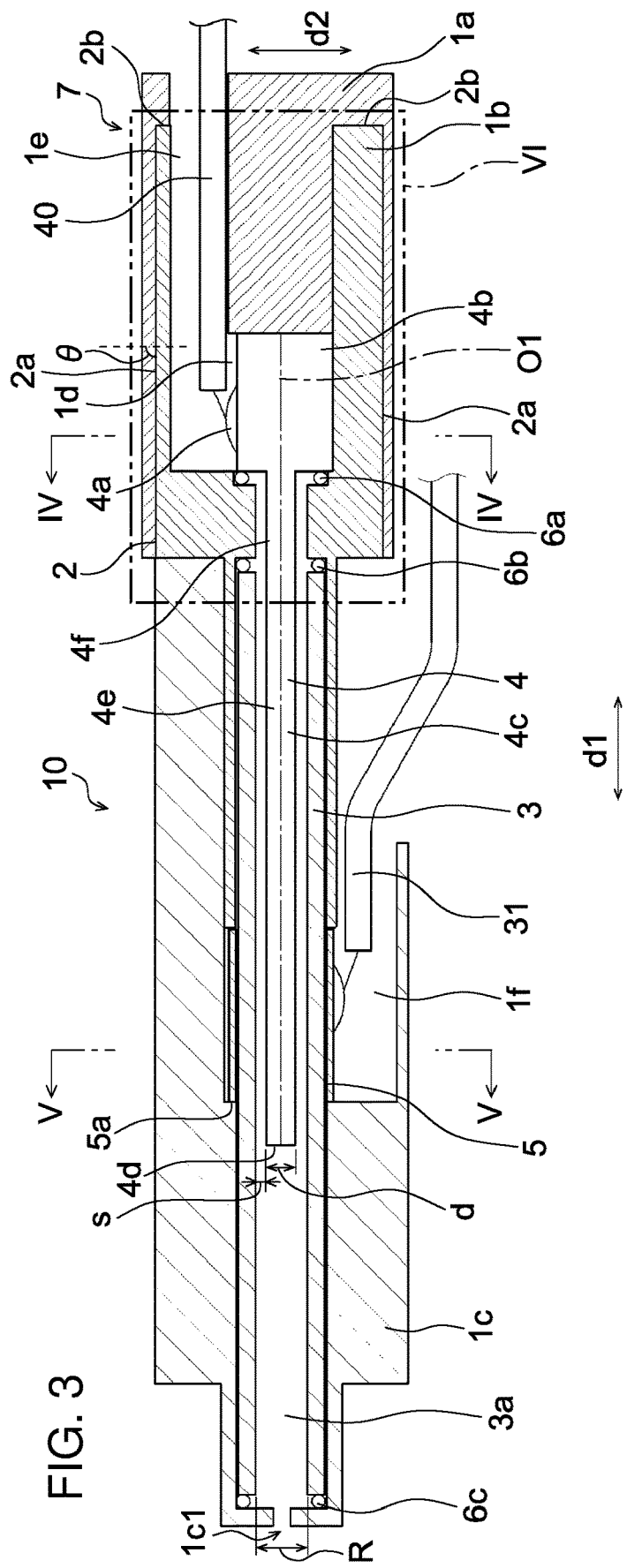
FIG. 3 is a sectional view of an irradiator according to the embodiment of the present invention.
Figure 4:
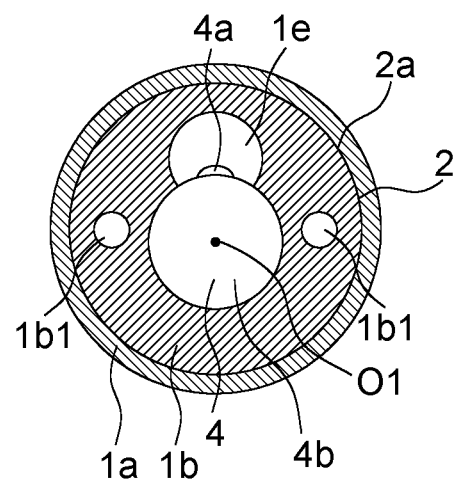
FIG. 4 is a sectional view of the irradiator of FIG. 3 taken along a IV-IV line.
Figure 5:
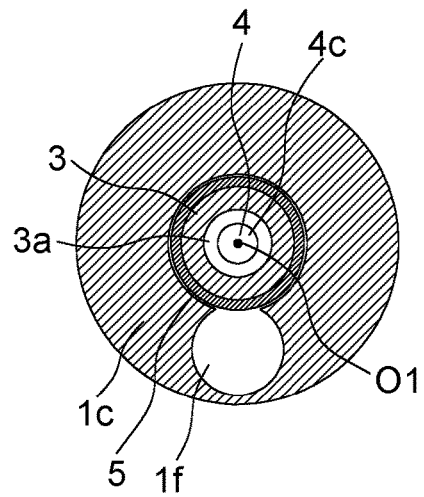
FIG. 5 is a sectional view of the irradiator of FIG. 3 taken along a V-V line.

FIG. 3 is a view showing the irradiator 10, which is a sectional view (longitudinal sectional view) of a plane along a direction in which the irradiator 10 extends. FIG. 4 is a sectional view showing a section taken along a IV-IV line of FIG. 3. FIG. 5 is a sectional view showing a section of the irradiator 10 taken along a V-V line of FIG. 3. In FIGS. 3 to 5, illustration of the outer cylinder member 8 and the nozzle 9 is omitted. As shown in FIG. 3, the irradiator 10 comprises an electrode holder 7. As shown in FIGS. 3 to 5, the electrode holder 7 comprises a first electrode 4, and a holding member 1 that holds the first electrode 4. In the example shown in FIG. 3, the electrode holder 7 further comprises a second electrode 5, a tubular dielectric 3, and O-rings 6a, 6b, 6c.

Figure 6:
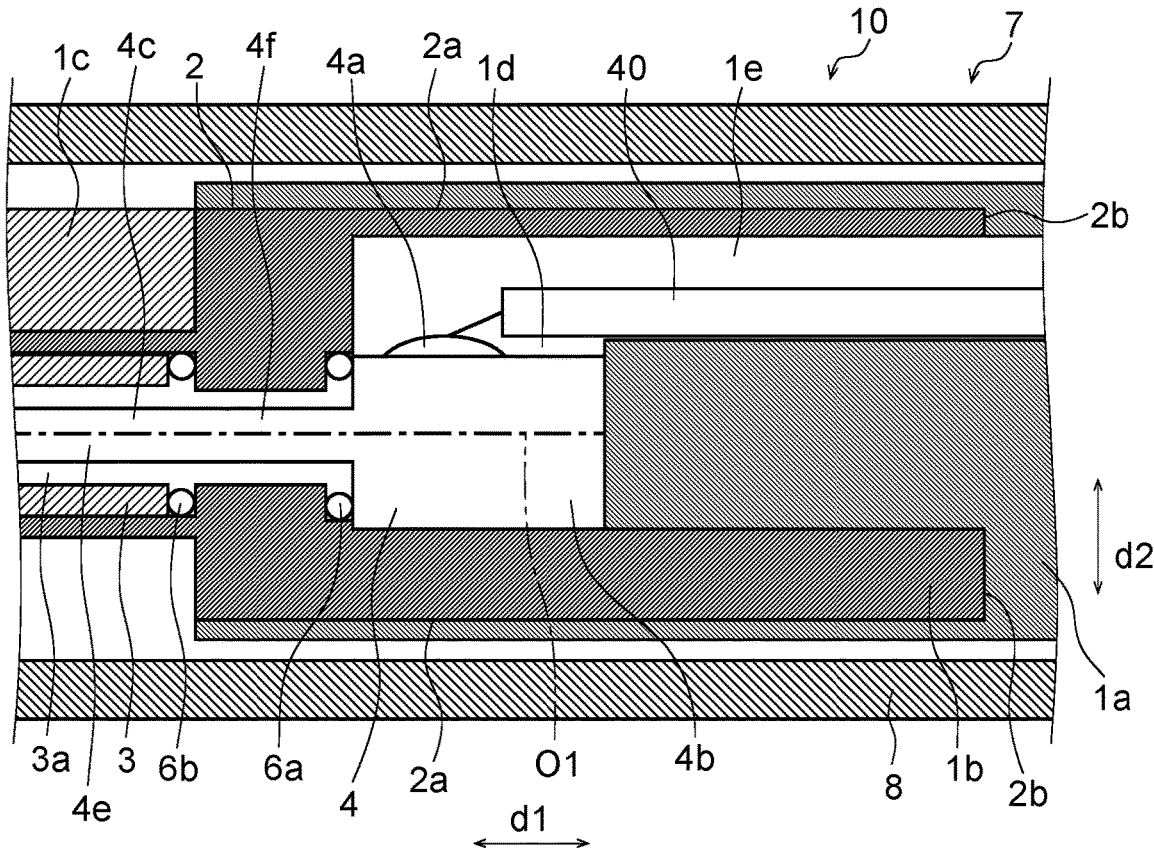
FIG. 6 is a partial sectional view of the irradiator according to the embodiment of the present invention.

In addition, as described above, the irradiator 10 may comprise the electrically grounded outer cylinder member 8, in addition to the electrode holder 7. FIG. 6 is a view showing a range of the irradiator 10 further comprising the outer cylinder member 8 in addition to the electrode holder 7 shown in FIG. 3, the range being surrounded by two-dot chain lines indicted by a reference numeral VI in FIG. 3. For example, the outer cylinder member 8 is an electrically conductive member having a substantially cylindrical shape, and accommodating the first electrode 4 entirely. The outer cylinder member 8 may accommodate the electrode holder 7 entirely. In the example shown in FIG. 6, the outer cylinder member 8 accommodates therein the electrode holder 7. Since the irradiator 10 has the outer cylinder member 8, an electric field generated by the irradiator 10 can be reduced to effectively prevent electric shock to a user handling the irradiator 10.

The first electrode 4 is an electrode to which a voltage is applied for generating a plasma. In the example shown in FIGS. 3 and 4, the first electrode 4 has a terminal 4a connected to an external power source through the voltage supply line 40. Thus, a voltage is applied to the first electrode 4 by the external power source. For example, when the voltage supply line 40 is soldered to the first electrode 4, the soldered portion serves as the terminal 4a.

As shown in FIG. 3, the first electrode 4 has an axis O1. The axis O1 of the first electrode 4 is, for example, a virtual line segment which extends in a direction d1 along which the first electrode 4 extends, and is located within a range where the first electrode 4 is located in the direction d1. Herebelow, the direction d1 along which the axis O1 extends is also referred to as axial direction d1.

In addition, the first electrode 4 has a larger diameter part 4*b* which has a largest outward projection length in a radial direction d2 perpendicular to the axis O1. In the example shown in FIG. 3, the first electrode 4 has a larger diameter part 4*b* and a narrower part 4*c* which has a smaller outward projection length in the radial direction d2 than the larger diameter part 4*b*. A part of the larger diameter part 4*b* is connected to the external power source to serve as the terminal 4*a*. In the example shown in FIGS. 3 to 5, the larger diameter part 4*b* and the narrower part 4*c* respectively have a substantially columnar shape extending in the axial direction d1.

An external diameter d of a part of the first electrode 4, which part is opposed to the second electrode 5 described later, can be suitably determined in consideration of intended use of the active gas irradiation apparatus 100 (namely, a size of the irradiator 10). When the active gas irradiation apparatus 100 is an intraoral treatment tool, the external diameter d is preferably between 0.5 mm and 20 mm, more preferably between 1 mm and 10 mm. When the outer diameter d is equal to or more than the above lower limit value, the first electrode 4 is easy to manufacture. In addition, when the external diameter d is equal to or more than the above lower limit value, a surface area of the first electrode 4 increases so that a plasma can be more efficiently generated to promote cure. When the external diameter d is equal to or less than the above upper limit value, a plasma can be more efficiently generated to further promote cure, without making excessively larger the irradiator 10.

A material of the first electrode 4 is not specifically limited as long as it is an electrically conductive material, and a metal used for an electrode of a known plasma apparatus can be used. The material of the first electrode 4 may be, for example, a metal such as stainless steel, copper, tungsten, or carbon, etc.

A voltage applied to the first electrode 4 is not specifically limited as long as it enables generation of a plasma between the first electrode 4 and the second electrode 5. When a plasma is generated by using a gas containing nitrogen as a main component described later, a voltage applied to the first electrode 4 is, for example, between 0.5 kVpp or more and 20 kVpp or less. The voltage applied to the first electrode 4 is more preferably between 2 kVpp or more and 18 kVpp or less, and furthermore preferably between 5 kVpp or more and 15 kVpp or less. Note that "pp" in "kVpp" is an abbreviation for "peak to peak".

The second electrode 5 is an electrode that is opposed to a part of the first electrode 4. In the example shown in FIGS. 3 and 5, the second electrode 5 is a cylindrical electrode that surrounds a part of the circumference of the first electrode 4. In the example shown in FIGS. 3 and 5, the second electrode 5 is opposed to a part of the narrower part 4*c* of the first electrode 4 in the radial direction d2. In this embodiment, the second electrode 5 is electrically grounded. In the example shown in FIG. 3, the second electrode 5 is connected to the ground wire 31 so as to be electrically grounded. By supplying a plasma generation gas to a space between the first electrode 4 and the second electrode 5 and by applying a voltage to the first electrode 4 opposed to the second electrode 5, the plasma generation gas can be ionized to generate a plasma.

An effect obtained by the fact that the second electrode 5 is opposed to a part of the first electrode 4 is described.

Suppose that the length of the second electrode 5 in the axial direction d1 is larger than the length of the first electrode 4 in the axial direction d1, and that the second electrode 5 is opposed to the entire first electrode 4 in the axial direction d1. In this case, a surface area of the first electrode 4, which is opposed to the second electrode 5, becomes larger. The larger the surface area of the electrode to be used, the higher a temperature of the plasma to be generated. Thus, when the second electrode 5 is opposed to the entire first electrode 4, the plasma to be generated has a higher temperature.

On the other hand, when the second electrode 5 is opposed to a part of the first electrode 4, the plasma to be generated can be suppressed to have a high temperature. Thus, a plasma having a lower temperature can be generated, which is suitable for irradiation of teeth, skin, etc. of humans and animals, for example. In particular, even when a higher voltage is applied to the electrode, the plasma to be generated is suppressed to have a high temperature. Thus, it can be said that an embodiment in which the second electrode 5 is opposed to a part of the first electrode 4 is particularly suitable for a case in which a high voltage is applied to the electrode.

In the example shown in FIG. 3, a distal end 4*d* of the first electrode 4 more projects to the distal side (left side in FIG. 3) of the irradiator 10 than a distal end 5*a* of the second electrode 5. Thus, a plasma can be stably generated along the total length of the second electrode 2 in the axial direction d1.

A material of the second electrode 5 is not specifically limited as long as it is an electrically conductive material, and a metal used for an electrode of a known plasma apparatus can be used. The material of the second electrode 5 may be, for example, a metal such as stainless steel, copper, tungsten, or carbon, etc.

The tubular dielectric 3 is a member having an inner hollow 3*a*. In the example shown in FIGS. 3 and 5, the tubular dielectric 3 is a cylindrical member extending in the axial direction d1. As shown in FIGS. 3 and 5, the first electrode 4 is located in the inner hollow 3*a* of the tubular dielectric 3. In the example shown in FIGS. 3 and 5, a part of the narrower part 4*c* of the first electrode 4 is located in the inner hollow 3*a*.

In the example shown in FIGS. 3 and 5, the first electrode 4 is located apart from an inner surface of the tubular dielectric 3. The second dielectric 5 is located in contact with an outer surface of the tubular dielectric 3.

A dielectric material used for a known plasma apparatus can be used as a material of the tubular dielectric 3. The material of the dielectric material 3 is, for example, glass, ceramic, synthetic resin, etc. The lower the dielectric constant of the tubular dielectric 3, the better.

An internal diameter R of the tubular dielectric 3 can be suitably determined in consideration of an external diameter d of the part of the first electrode 4, which part is opposed to the second electrode 5 described later. The internal diameter R is determined such that a distance s described later is within a desired range.

In a case where the first electrode 4 and the tubular dielectric 3 are spaced apart from each other, the distance s between the outer surface of the first electrode 4 and the inner surface of the tubular dielectric 3 is preferably between 0.05 mm and 5 mm, more preferably between 0.1 mm and 1 mm. When the distance s is equal to or more than the above lower limit value, it is easy for a plasma generation gas of a desired volume to flow therethrough, when the inner hollow 3*a* of the tubular dielectric 3 is used as a flow channel of the plasma generation gas as described later. When the distance s is equal to or less than the above upper limit value, a plasma can be more efficiently generated so that a temperature of an active gas can be lowered.

The holding member 1 is a member that holds an electrode. For example, the holding member 1 electrically insulates the first electrode 4. For example, as shown in FIG. 3, the holding member 1 holds the first electrode 4 in contact with the first electrode 4. For example, the holding member 1 holds the first electrode 4 directly facing the first electrode 4. In other words, an area in which another member is not located is at least partially formed between the holding member 1 and the first electrode 4. As shown in FIG. 3, the holding member 1 has a first member 1a and a second member 1b. The first member 1a and the second member 1b are in contact with each other so as to form an accommodation space 1d that accommodates at least a part of the first electrode 4. In the example shown in FIG. 3, the larger diameter part 4b of the first electrode 4 is accommodated in the accommodation space 1d.

Figure 7:
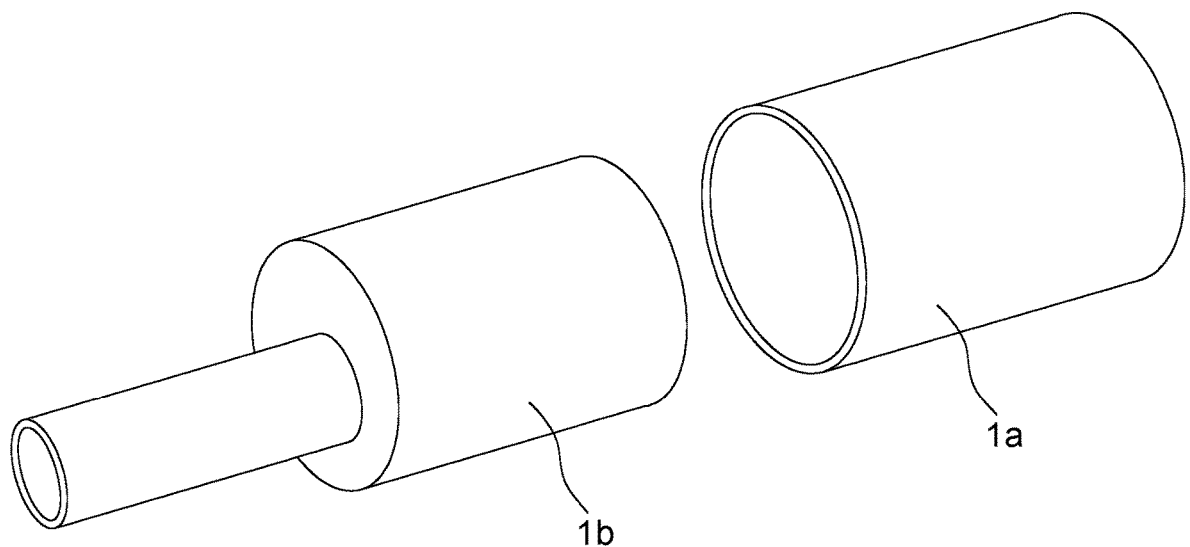
FIG. 7 is a perspective view of a first member and a second member of a holding member according to the embodiment of the present invention.

FIG. 7 is a perspective view showing the first member 1a and the second member 1b. In FIG. 7, illustration of screw holes used for fixing the first member 1a and the second member 1b to each other is omitted. In the example shown in FIGS. 3 and 7, both the first member 1a and the second member 1b are substantially cylindrical members extending in the axial direction d1. In the example shown in FIGS. 3 and 7, the second member 1b has a shape which allows at least a part thereof to be inserted to the first member 1a. Specifically, the second member 1b has an external diameter which is at least partially smaller than an internal diameter of the first member 1a. By inserting a part of the second member 1b to the first member 1a, the first member 1a and the second member 1b come into contact with each other to form the accommodation space 1d. Although not shown, at least a part of the first member 1a may be inserted to the second member 1b so that the first member 1a and the second member 1b come into contact with each other to form the accommodation space 1d.

In the example shown in FIG. 4, the second member 1b is provided with screw holes 1b1 to which screws are inserted. Although not shown, the first member 1a is also provided with screw holes. The first member 1a and the second member 1b are fixed to each other while being in contact with each other by screw, not shown, inserted in the screw holes of the first member 1a and the second member 1b.

In the example shown in FIG. 3, the first member 1a is in contact with the first electrode 4 from one side (right side in FIG. 3) along the axis O1 to restrict movement of the first electrode 4 to the one side along the axis O1. In addition, the second member 1b is in contact with the first electrode 4 from the other side (left side in FIG. 3) along the axis O1 to restrict movement of the first electrode 4 to the other side along the axis O1. In the example shown in FIG. 3, the second member 1b is in contact with the larger diameter part 4b of the first electrode 4 through the O-ring 6a from the other side along the axis O1. The O-ring 6a is a member made of a resilient resin member. The O-ring 61 is sandwiched between the larger diameter part 4b and the second member 1b to be in tight contact with the larger diameter part 4b and the second member 1b. Thus, the first electrode 4 is held with its movement along the axial direction d1 being restricted.

The second electrode 5 and the tubular dielectric 3 are attached to the holding member 1. In the example shown in FIG. 3, the holding member 1 further has the third member 1c. The holding member 1 further holds the second electrode 5 and the tubular dielectric 3 by the second member 1b and the third member 1c. In the example shown in FIG. 3, the third member 1c is a substantially cylindrical member extending in the axial direction d1. In the example shown in FIG. 3, the second member 1b has a shape which allows at least a part thereof to be inserted to the third member 1c. Specifically, the second member 1b has the external diameter which is at least partially smaller than an internal diameter of the third member 1c. By inserting a part of the second member 1b to the third member 1c, the second member 1b and the third member 1c come into contact with each other to form a space in which the second electrode 5 and the tubular dielectric 3 are accommodated. Although not shown, at least a part of the third member 1c may be inserted to the second member 1b so that the second member 1b and the third member 1c come into contact with each other to form the space in which the second electrode 5 and the tubular dielectric 3 are accommodated.

The second member 1b is in contact with the second electrode 5 from the one side along the axis O1 to restrict movement of the second electrode 5 to the one side along the axis O1. In addition, the third member 1c is in contact with the second electrode from the other side along the axis O1 to restrict movement of the second electrode 5 to the other side along the axis O1. Thus, the second electrode 5 is held with its movement along the axial direction d1 being restricted.

Further, the second member 1b is in contact with the tubular dielectric 3 through the O-ring 6b from the one side along the axis O1 to restrict movement of the tubular dielectric 3 to the one side along the axis O1. The third member 1c is in contact with the tubular dielectric 3 through the O-ring 6c from the other side along the axis O1 to restrict movement of the tubular dielectric 3 to the other side along the axis O1. Each of the O-rings 6b, 6c is a member made of a resilient resin member, and has an internal diameter which allows the O-ring 6b, 6c to be in tight contact with the outer circumferential surface of the tubular dielectric 3. Thus, the tubular dielectric 3 is held with its movement along the axial direction d1 being restricted.

The irradiation opening 1c1 is provided in the distal end of the third member 1c in the distal end side (left side in FIG. 3) of the irradiator 10. In the example shown in FIG. 3, the irradiation opening 1c1 communicates the inner hollow 3a of the tubular dielectric 3 with the outside of the irradiator 10.

In the example shown in FIGS. 3 and 4, the holding member 1 further has a voltage-supply-line accommodation part 1e that accommodates a part of the voltage supply line 40 in such a manner that the voltage supply line 40 can be connected to the terminal 4a and can extend to the outside of the holding member 1. In the example shown in FIGS. 3 and 5, the holding member 1 further has a ground-wire accommodation part 1f that accommodates a part of the ground wire 31 in such a manner that the ground wire 31 can be connected to the second electrode 5 and can extend to the outside of the holding member 1.

In the example shown in FIGS. 3 to 7, the first member 1a, the second member 1b, and the third member 1c have a substantially circular cylindrical shape. Although not shown, the first member 1a, the second member 1b, and the third member 1c may have a polygonal cylindrical shape, such as a quadrangular cylindrical shape, a hexagonal cylindrical shape, an octagonal cylindrical shape, etc.

A material of the first member 1a, the second member 1b, and the third member 1c is not specifically limited, but an insulating material is preferred. The insulating material is, for example, a thermoplastic resin, a thermosetting resin, etc. The thermoplastic resin is, for example, polyethylene, polypropylene, polyvinyl chloride, polystyrene, acrylonitrile-butadiene-styrene resin (ABS resin), polyether ether ketone (PEEK), polytetrafluoroethylene (PTFE), polyvinylidene fluoride (PVDF), polyethyleneimine (PEI), polyacetal (POM), modified polyphenylene ether (mPPE), etc. The thermosetting resin is, for example, phenol resin, melamine resin, urea resin, epoxy resin, unsaturated polyester resin, silicone resin, etc. In addition, an insulating material made by filling polyethylene terephthalate (PET) as a main component with short glass fibers and/or inorganic fillers may be used. Such a material may be Unilate (registered trademark) manufactured by Unitika, Ltd. PEEK or mPPE is more preferable as a material of the first member 1a, the second member 1b, and the third member 1c, because of their resin properties suitable for the first member 1a, the second member 1b, and the third member 1c.

Since the holding member 1 includes the first member 1a and the second member 1b, and further includes the third member 1c, the holding member 1 can be divided into a plurality of members. Thus, the first electrode 4, the second electrode 4, the tubular dielectric 3, etc., which are held by the holding member 1, can be easily detached from the holding member 1. In addition, it is easy to assemble the electrode holder 7 and the irradiator 10 with the use of the first member 1a, the second member 1b, and the third member 1c.

The irradiator 10 shown in FIG. 3 can be assembled by the following procedure, for example. First, the first member 1a, the second member 1b, and the first electrode 4 are located such that the first member 1a and the second member 1b are opposed to each other with the first electrode 4 therebetween.

Then, the first member 1a and the second member 1b are brought into contact with each other in such a manner that at least a part of the first electrode 4 is accommodated in the accommodation space 1d, and the first member 1a and the second member 1c are fixed to each other. Particularly in the case of the irradiator 10 shown in FIG. 3, the first electrode 4 is inserted into the first member 1a from the larger diameter part 4b side in such a manner that at least the larger diameter part 4b is located inside the first member 1a, and that at least a part of the narrower part 4c is located outside the first member 1a. Thus, the first electrode 4 and the first member 1a are in contact with each other in the axial direction d1, so that movement of the first electrode 4 is suppressed. Then, the first member 1a and the second member 1b are brought into contact with each other and are fixed to each other, by bringing the second member 1b close to the first member 1a from the narrower part 4c of the first electrode 4, in such a manner that the narrower part 4c passes through the second member 1b and that the second member 1b covers the larger diameter part 4b. Thus, the first electrode 4 is held by the first member 1a and the second member 1b.

Then, the third member 1c, the second electrode 5, and the tubular dielectric 3 are located in such a manner that the second member 1b and the third member 1c are opposed to each other with the second electrode 5 and the tubular dielectric 3 therebetween. Then, the second member 1b and the third member 1c are brought into contact with each other and are fixed to each other in such a manner that the second electrode 5 and the tubular dielectric 3 are accommodated between the second member 1b and the third member 1c.

The irradiator 10 according to this embodiment can be assembled by the above procedure. When the first member 1a and the second member 1b are brought into contact with each other, interference between the first electrode 4 and the second member 1b is suppressed, which results in the improved ease of assembly.

As shown in FIGS. 3 and 4, a contact surface 2 between the first member 1a and the second member 1b includes a non-perpendicular contact surface 2a that is non-perpendicular to the axis O1. In the example shown in FIG. 3, the contact surface 2 includes a perpendicular contact surface 2b that is perpendicular to the axis O1, in addition to the non-perpendicular contact surface 2a.

As shown in FIG. 3, the non-perpendicular contact surface 2a is located outside the first electrode 4 in the radial direction d2. In the example shown in FIG. 3, an angle θ defined by the non-perpendicular contact surface 2a with respect to the radial direction d2 is 90°. As described above, since a part of the second member 1b is inserted to the first member 1a so that the contact surface 2 between the first member 1a and the second member 1b is formed, the non-perpendicular contact surface 2a surrounds the first electrode 4 from a circumference about the axis O1, as shown in FIG. 4.

Figure 8:
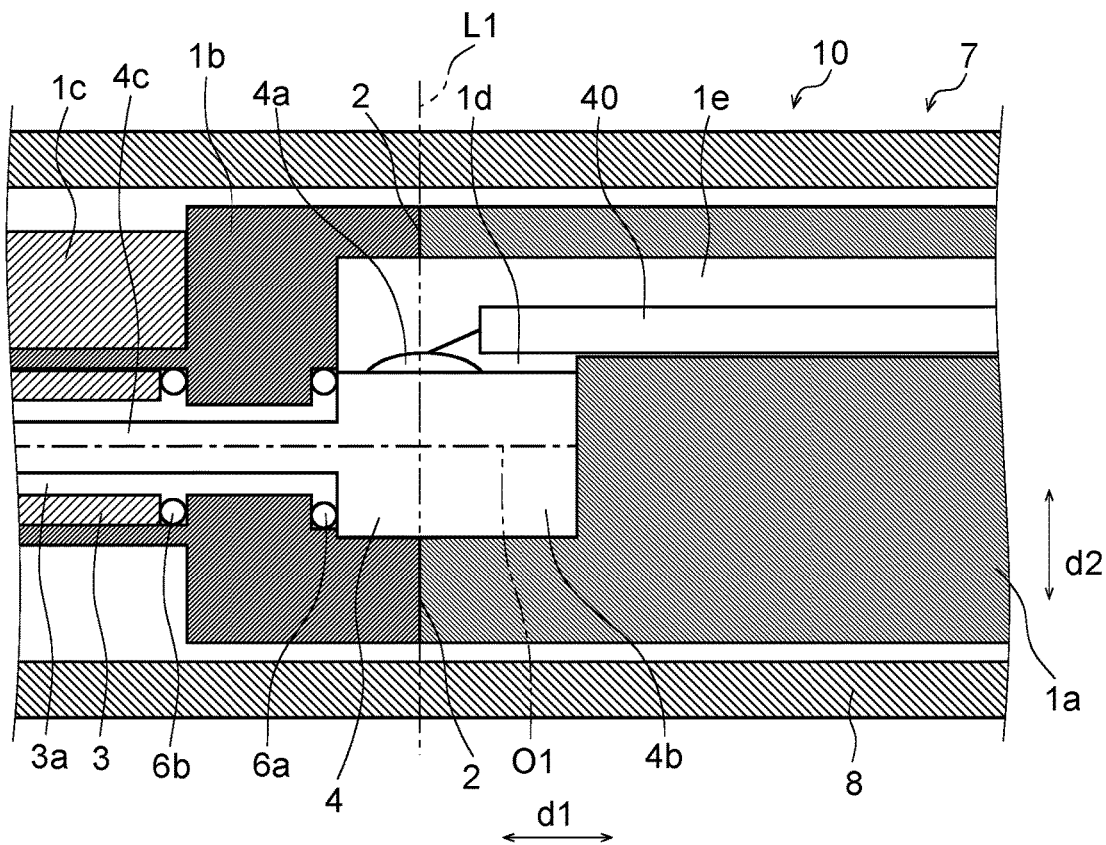
FIG. 8 is a partial sectional view of the irradiator according to a reference example.

An effect obtained by the contact surface 2 including the non-perpendicular contact surface 2a is described in comparison with a reference example. First, a reference example in which the contact surface 2 does not include the non-perpendicular contact surface 2a is considered. FIG. 8 is a sectional view showing a circumference of the contact surface 2 of the irradiator 10 comprising the electrode holder 7 and the outer cylinder member 8, according to the reference example. An electrically conductive object, such as the outer cylinder member 8 shown in FIG. 8, may be located outward the first electrode 4 in the radial direction d2 and outside the holding member 1. The contact surface 2 according to the reference example does not have the non-perpendicular contact surface 2a and thus is a surface perpendicular to the axis O1. In this case, there is a perpendicular L1 which is perpendicular to the axis O1 and is located on the contact surface 2. Along the perpendicular L1, an electric line of force, which moves from the first electrode 4 to which a voltage is applied to the object outside the holding member 1, is not interrupted by the first member 1a and the second member 1b. Thus, there is a possibility that a short circuit occurs between the first electrode 4 and the object outside the holding member 1, by means of creeping discharge through a space between the first member 1a and the second member 1b. The short circuit may damage and impair the irradiator 10.

On the other hand, the contact surface 2 according to this embodiment includes the non-perpendicular contact surface 2a. In the example shown in FIGS. 3 and 6, the non-perpendicular contact surface 2a is provided in such a manner that a perpendicular to the axis O1 includes a line crossing the non-perpendicular contact surface 2a. Since the contact surface 2 includes the non-perpendicular contact surface 2a, an electric line of force, which extends from the first electrode 4 in the radial direction d2 toward the object outside the holding member 1, is interrupted by the first member 1a and the second member 1b, at a position where the non-perpendicular contact surface 2a is located outward the first electrode 4 in the radial direction d2. Thus, a creeping distance between the first electrode 4 and the object outside the holding member 1 can be elongated, whereby a short circuit between the first electrode 4 and the object outside the holding member 1 through a space between the first member 1a and the second member 1b is suppressed. In particular, a short circuit through a space between the first member 1a and the second member 1b can be suppressed, while facilitating disassembly and assembly of the holding member 1.

In the example shown in FIG. 6, the non-perpendicular contact surface 2a is located between the first electrode 4 and the outer cylinder member 8. Thus, a short circuit between the first electrode 4 and the outer cylinder member 8 through a space between the first member 1a and the second member 1b can be suppressed.

In this embodiment, the non-perpendicular contact surface 2a is provided in such a manner that any perpendiculars to the axis O1 through the non-perpendicular contact surface 2a is non-parallel to the non-perpendicular contact surface O1. In other words, in this embodiment, the non-perpendicular contact surface 2a is provided in such a manner that, when a perpendicular to the axis O1 through the non-perpendicular contact surface 2a is drawn, the perpendicular is invariably non-parallel to the non-perpendicular contact surface 2a, and it is impossible to draw a perpendicular parallel to the non-perpendicular contact surface 2a. Thus, an electric line of force, which moves from the first electrode 4 to the object outside the holding member 1, is interrupted by the first member 1a and the second member 1b, along a line which is a perpendicular to the axis O1 through the non-perpendicular contact sauce 2a. Thus, a short circuit between the first electrode 4 and the object outside the holding member 1 through a space between the first member 1a and the second member 1b can be suppressed.

A component for connecting the first electrode 4 to the external power source, such as a solder and/or a part of the voltage supply line 40 to be soldered to the first electrode 4, may be disposed on the terminal 4a of the first electrode 4. Thus, a distance between the first electrode 4 and the component electrically connected to the first electrode 4, and the object outside the holding member 1 is likely to be short, because of the component disposed on the terminal 4a for connecting the first electrode 4 to the external power source, which may invite a short circuit. In the example shown in FIGS. 3, 4 and 6, the non-perpendicular contact surface 2a is located outside the terminal 4a in the radial direction. This can effectively suppress a short circuit between the terminal 4a and the object outside the holding member 1.

The larger diameter part 4b of the first electrode 4 is a portion of the first electrode 4, which has a largest length projecting outward in the radial direction d2. Thus, a distance between the larger diameter part 4b and the object outside the holding member 1 is likely to be short, which may invite a short circuit. In the example shown in FIGS. 3, 4 and 6, the non-perpendicular contact surface 2a is located outside the larger diameter part 4b in the radial direction d2. This can effectively suppress a short circuit between the larger diameter part 4b and the object outside the holding member 1.

In the example shown in FIG. 3, the second electrode 5 is opposed to a part of the first electrode 4. As compared with the part of the first electrode 4 which is opposed to the object outside the holding member 1, another part of the first electrode 4, which is not opposed to the second electrode 5, is considered to be more likely to occur a short circuit with the object outside the holding member 1, because of absence of the second electrode 5 therebetween. In the example shown in FIG. 3, the non-perpendicular contact surface 2a is located in an area different from an area in which the second electrode 5 is located in a direction along which the axis O1 extends. This can effectively suppress a short circuit between the part of the first electrode 4, which is not opposed to the second electrode 5, and the object outside the holding member 1.

In the example shown in FIG. 3, a part of the first electrode 4 is located in the inner hollow 3a of the tubular dielectric 3. In the example shown in FIG. 3, the non-perpendicular contact surface 2a is located in an area different from an area in which the tubular dielectric 3 is located in a direction along which the axis O1 extends.

In the example shown in FIG. 4, as described above, the non-perpendicular contact surface 2a surrounds the first electrode 4 from a circumference about the axis O1. This can suppress a short circuit between the first electrode 4 and the object outside the holding member 1 in the entire circumferential direction about the axis O1.

In the example shown in FIGS. 3 and 6, the contact surface includes the perpendicular contact surface 2b. Suppose that the perpendicular contact surface 2b is located in an area in which the first electrode 4 is located in the axial direction d1. In this case, in the area in which the perpendicular contact surface 2b is located, the thickness of the holding member 1 that interrupts an electric line of force, which extends from the first electrode 4 in the radial direction d2 toward the object outside the holding member 1, decreases.

On the other hand, in the example shown in FIGS. 3 and 6, the perpendicular contact surface 2b is located in an area different from an area in which the terminal 4a is located in the axial direction d1. Thus, the thickness of the area of the holding member 1, in which area the terminal 4a is located, can be ensured. Thus, even when a high voltage is applied to the first electrode 4, a short circuit between the terminal 4a and the object outside the holding member 1 through a part of the holding member 1, in which part the holding member 1 has a reduced thickness, can be suppressed.

In the example shown in FIGS. 3 and 6, the perpendicular contact surface 2b is located in an area different from an area in which the larger diameter part 4b is located in the axial direction d1. This can suppress a short circuit between the terminal 4a and the object outside the holding member 1 through a part of the holding member 1, in which part the holding member 1 has a reduced thickness.

In the example shown in FIGS. 3 and 6, the first electrode 4 has a first portion 4e which is located in the inner hollow 3a of the tubular dielectric 3, and a second portion 4f which is located outside the inner hollow 3a. The perpendicular contact surface 2b is located in an area different from an area in which the second portion 4f is located in the axial direction d1.

In the example shown in FIGS. 3 and 6, the perpendicular contact surface 2b is located in an area different from an area in which the first electrode 4 is located in the axial direction d1. This can ensure the thickness of the holding member 1 in the entire area in which the second electrode 4 is located. This can suppress a short circuit between the terminal 4a and the object outside the holding member 1 through a part of the holding member 1, in which part the holding member 1 has a reduced thickness.

In the irradiator 10, a plasma generation gas is supplied from the supply unit 20 to a space between the first electrode 4 and the second electrode 5. In the example shown in FIGS. 3 and 5, the first electrode 4 and the tubular dielectric 3 are spaced apart from each other. In this case, the inner hollow 3a of the tubular dielectric 3 may be used as a flow channel for the plasma generation gas to supply the plasma generation gas to a space between the first electrode 4 and the second electrode 5. Although not shown, when the second electrode 5 is spaced apart from the tubular dielectric 3, an interval between the second electrode 5 and the tubular dielectric 3 may be used as a flow channel for the plasma generation gas to supply the plasma generation gas to a space between the first electrode 4 and the second electrode 5.

A method of supplying the plasma generation gas to a space between the first electrode 4 and the second electrode 5 is not specifically limited. Although not shown, the inside of the first electrode 4 may be hollow. In this case, the plasma generation gas supplied to the irradiator 10 through the gas pipeline 30 passes through the inside of the first electrode 4 to exit from a hole of the first electrode 4, which is provided in a part opposed to the second electrode 5, so as to be supplied to a space between the first electrode 4 and the second electrode 5. Alternatively, a though hole may be provided in the holding member described later. In this case, the plasma generation gas supplied to the irradiator 10 through the gas pipeline 10 is supplied to a space between the first electrode 4 and the second electrode 5 through the through hole of the holding member 1.

The supply unit 20 as shown in FIG. 1 supplies the irradiator 10 with electricity and the plasma generation gas. The supply unit 20 can regulate a voltage and a frequency to be applied to a space between the first electrode 4 and the second electrode 5. The supply unit 20 comprises a housing 21 that accommodates the supply source 70. The housing 21 removably accommodates the supply source 70. Thus, when the supply source 70 accommodated in the housing 21 runs out of a gas, the supply source 70 of the plasma generation gas can be replaced with another supply source 70.

The supply source 70 supplies a plasma generation gas to a space between the first electrode 4 and the second electrode 5. The supply source 70 is a pressure-resistant container that contains the plasma generation gas. As shown in FIG. 2, the supply source 70 is detachably mounted on a pipe 75 located in the housing 21. The pipe 75 connects the supply source 70 and the gas pipeline 30. A solenoid valve 71, a pressure regulator 73, a flowrate controller 74, and a pressure sensor 72 (remaining volume sensor) are attached to the pipe 75.

When the solenoid valve 71 is opened, the plasma generation gas is supplied from the supply source 70 to the irradiator 10 through the pipe 75 and the gas pipeline 30. In the illustrated example, an opening degree of the solenoid valve 71 cannot be adjusted, and the solenoid valve 71 is merely turned on or off. However, an opening degree of the solenoid valve 71 may be adjusted. The pressure regulator 73 is located between the solenoid valve 71 and the supply source 70. The present regulator 73 reduces a pressure of the plasma generation gas (depressurizes the plasma generation gas) moving from the supply source 70 toward the solenoid valve 71.

The flowrate controller 74 is located between the solenoid valve 71 and the gas pipeline 30. The flowrate controller 74 regulates a flowrate (supply volume per unit time) of the plasma generation gas having passed through the solenoid valve 71. The flowrate controller 74 regulates a flowrate of the plasma generation gas to 3 L/min, for example.

The pressure sensor 72 detects a remaining volume V1 of the plasma generation gas in the supply source 70. The pressure sensor 72 measures a pressure (remaining pressure) in the supply source 70 as a remaining volume V1. The pressure sensor 72 measures, as a pressure of the supply source 70, a pressure (primary pressure) of the plasma generation gas passing through between the pressure regulator 73 and the supply source 70 (closer to the primary side than the pressure regulator 73). AP-V80 series of KEYENCE Co. (specifically, AP-15S) can be employed as the pressure sensor 72, for example.

An actual remaining volume V1 (cubage) in the supply source 70 is calculated from a remaining pressure measured by the pressure sensor 72 and a capacity (internal volume) of the supply source 70. When a supply source 70 of various capacities are used, a capacity for calculation may be set by selecting an actual capacity of the supply source 70 on a system screen of an input unit, not shown. Alternatively, when a supply source 70 of a constant capacity is used, the control unit 90 may store its capacity in advance.

A joint 76 is provided on an end of the pipe 75, which end is on a side of the supply source 70. The supply source 70 is detachably mounted on the joint 76. By detaching and attaching the joint 76 from and to the supply source 70, the supply source 70 of the plasma generation gas can be replaced with another one, while the solenoid valve 71, the pressure regulator 73, the flowrate controller 74, and the pressure sensor 72 (referred to as "solenoid valve 71 and so on" herebelow) remain fixed in the housing 21. In this case, the solenoid valve 71 and so on can be shared between the current supply source 70 and the replaced supply source 70. The solenoid valve 71 and so on may be fixed to the supply source 70 so as to be detached from the housing 21 together with the supply source 70.

As shown in FIG. 1, the gas pipeline 30 is a channel through which the plasma generation gas is supplied from the supply unit 20 to the irradiator 10. The gas pipeline 30 is connected to a rear end of the tubular dielectric 3 of the irradiator 10. A material of the gas pipeline 30 is not specifically limited, and a material used for a known gas pipe can be used. The gas pipeline 30 may be a resin pipe or a rubber tube, for example. A flexible material is preferred as a material of the gas pipeline 30.

The voltage supply line 40 is a line that supplies a voltage from the supply unit 20 to the irradiator 10. The voltage supply line 40 is connected to the first electrode 4 of the irradiator 10, as described above, and is connected to a foot switch, not shown. A material of the voltage supply line 40 is not specifically limited, and a material used for a known voltage supply line can be used. The voltage supply line 40 may be a metal conducive wire covered with an insulating material.

The control unit 90 as shown in FIG. 2 is formed of an information processing device. Namely, the control unit 90 comprises a CPU (Central Processer Unit), a memory, and an auxiliary storage device connected by a bus. The control unit 90 is operated by executing a program. The control unit 90 may be incorporated in the supply unit 20, for example. The control unit 90 controls the irradiator 10, the supply unit 20, and the notification unit 80.

A foot switch, not shown, is electrically connected to the control unit 90. When a user of the irradiator 10 operates the foot switch, an electric signal is transmitted from the foot switch to the control unit 90. When the control unit 90 receives the electric signal, the control unit 90 activates the solenoid valve 71 and the flowrate controller 74, and applies a voltage to the first electrode 4.

In this embodiment, every time a user presses the foot switch, the control unit 90 receives the electric signal. Then, the control unit 90 opens the solenoid valve 71 for a predetermined period of time, causes the flowrate controller 74 to regulate a flowrate of the plasma generation gas which has passed through the solenoid valve 71, and applies a voltage to the first electrode 4 for a predetermined period of time. As a result, a certain volume of the plasma generation gas is supplied from the supply source 70 to a space between the first electrode 4 and the second electrode 5, and an active gas is continuously ejected from the nozzle irradiation opening 9a for a certain period of time (e.g., from several seconds to several tens of seconds, 30 seconds in this embodiment).

Namely, in this embodiment, an ejection volume of the active gas per one press of the foot switch by a user is fixed. Such an operation for ejecting the active gas of the predetermined ejection volume is referred to as a unit operation. In this embodiment, the unit operation is one pressing of foot switch by a user. An ejection volume of the active gas per unit operation (a supply volume of the plasma generation gas from the supply source 70 to a space between the first electrode 4 and the second electrode 5 per unit operation) may be a fixed value that is previously set or a variable value that can be set by operating an operation panel, not shown.

The control unit 90 computes as remaining information at least one of a remaining number of times N and a remaining time T of the plasma generation gas. In this embodiment, the control unit 90 computes as the remaining information only the remaining number of times N among the remaining number of times N and the remaining time T. The remaining number of times N is a number of times of the unit operations to be left during which the plasma generation gas can be supplied from the supply source 70 to a space between the first electrode 4 and the second electrode 5. The remaining time T is a time to be left during which the plasma generation gas can be supplied from the supply source 70 to a space between the first electrode 4 and the second electrode 5.

Both the remaining time N and the remaining time T can be calculated from the remaining volume V1 of the plasma generation gas in the supply source. The remaining number of times N can be calculated (N=V1/V2) based on the remaining volume V1 and a supply volume V2 of the plasma generation gas per unit operation of the foot switch. Alternatively, the remaining number of times N is calculated by computing an average value V2 (average value) of usages (supplies) of the plasma generation gas over the last several times, and by dividing the remaining volume V1 of the plasma generation gas by the average value V2 (average value). The remaining time T can be calculated (T=V1/V3) based on the remaining volume V1, and a supply volume V3 of the plasma generation gas supplied from the supply source 70 to a space between the first electrode 4 and the second electrode 5 per unit time.

The notification unit 80 gives a notice of at least one of the remaining number of times N and the remaining time T. In this embodiment, the notification unit 80 displays the number of times N. The notification unit 80 displays the remaining number of times N calculated by the control unit 90 by a numeric character. A display unit capable of displaying a numeric character or a mechanical counter may be employed as the notification unit 80.

In the illustrated example, the notification unit 80 is integrated in the housing 21 on an outer surface thereof. However, the notification unit 80 may be independent from the supply unit 20. The notification unit 80 may display the remaining number of times N by a way different from a numerical character. For example, an analogue display structure formed of a dial and a needle may be employed as the notification unit 80. Further, the notification unit 80 may give a notice of the remaining number of times N by displaying a color or by turning on/off light.

Further, the notification unit 80 may give a notice of the remaining number of times N by sound. In this case, a speaker can be employed as the notification unit 80, for example.

As in this embodiment, when a certain volume of the plasma generation gas is supplied from the supply source 70 to a space between the first electrode 4 and the second electrode 5 upon pressing of the foot switch by a user, to give a notice of the remaining number of times N is more convenient for a user than to give a notice of the remaining time T.

Next, a method of using the active gas irradiation apparatus 100 is described. A user such as a doctor moves the irradiator 10 by hand and directs the nozzle irradiation opening 9a toward an irradiation target described later. Under this state, the user presses the foot switch to supply electricity and a plasma generation gas from the supply source 70 to the irradiator 10. The plasma generation gas supplied to the irradiator 10 flows from the rear end of the tubular dielectric 3 into the inner hollow 3a of the tubular dielectric 3. The plasma generation gas is ionized at a position where the first electrode 4 and the second electrode 5 are opposed to each other to become a plasma.

In this embodiment, the first electrode 4 and the second electrode 5 are opposed to each other in a direction orthogonal to the direction along which the plasma generation gas flows. The plasma, which was generated at the position where outer circumferential surface of the first electrode 4 and the inner circumferential surface of the second electrode 5 are opposed to each other, changes the composition of the gas to become an active gas containing active species such as radical, while flowing through the inner hollow 3a of the tubular dielectric 3.

The active gas thus generated is ejected from the nozzle irradiation opening 9a. The ejected active gas further activates a part of the gas near the nozzle irradiation opening 9a to generate active species. The active gas containing these active species is applied to the irradiation target.

The irradiation target may include, for example, cells, living tissues, biological individuals, etc. The living tissues may include, for example, respective organs such as viscera, epithelial tissues covering body surfaces and inner surfaces of body cavities, periodontal tissues such as gingiva, alveolar bone, periodontal ligament and cementum, teeth, bones, etc. The biological individuals may be any mammals such as humans, dogs, cats, pigs, etc.; birds; fish; etc.

The plasma generation gas may be, for example, rare gases such as helium, neon, argon, krypton, etc.; nitrogen, etc. One of these gases may be used solely or two or more gases may be used in combination. The plasma generation gas preferably contains nitrogen as a main component. Herein, a gas containing nitrogen as a main component means that a nitrogen content in the plasma generation gas is more than 50% by volume. Namely, the nitrogen content in the plasma generation gas is preferably more than 50% by volume, more preferably 70% by volume, and particularly preferably between 90% by volume and 100% by volume. A gas component in the plasma generation gas, other than nitrogen, is not specifically limited, and may be, for example, oxygen, rare gas, etc.

When the plasma generation gas contains nitrogen as a main component, a particularly high voltage is needed to generate a plasma. As described above, the invention according to the embodiment is suitable for a case in which a high voltage is applied to the electrode, because the second electrode 5 is opposed to a part of the first electrode 4. Thus, it can be said that the invention according to the embodiment is suitable for a case in which the plasma generation gas contains a nitrogen gas as a main component.

When the active gas irradiation apparatus 100 is an intraoral treatment tool, an oxygen concentration of the plasma generation gas to be introduced to the tubular dielectric 3 is preferably 1% by volume or less. When the oxygen concentration is equal to or less than the upper limit value, generation of ozone can be reduced.

A flowrate of the plasma generation gas to be introduced to the tubular dielectric 3 is preferably between 1 L/min and 10 L/min. When the flowrate of the plasma generation gas to be introduced to the tubular dielectric 3 is equal to or more than the lower limit value, increase in temperature of an irradiation surface of the irradiation target can be easily suppressed. When the flowrate of the plasma generation gas is equal to or less than the upper limit value, purification, activation or cure of the irradiation target can be further promoted.

A temperature of the active gas applied from the nozzle irradiation opening 9*a* is preferably 50° C. or less, more preferably 45° C. or less, further preferably 40° C. or less. When the temperature of the active gas applied from the nozzle irradiation opening 9*a* is equal to or less than the upper limit value, it is easy for the irradiation surface to have a temperature of 40° C. or less. When the irradiation surface has a temperature of 40° C. or less, stimulus to an affected area as the irradiation part can be reduced. A lower limit value of the temperature of the active gas applied from the nozzle irradiation opening 9*a* is not specifically limited, and is 10° C. or more, for example. The temperature of the active gas is a value of the temperature of the active gas, which is measured at the nozzle irradiation opening 9*a* by a thermocouple.

A distance (irradiation distance) from the nozzle irradiation opening 9*a* to the irradiation surface is preferably between 0.01 mm and 10 mm, for example. When the irradiation distance is equal to or more than the above lower limit value, the temperature of the irradiation surface can be lowered to further mitigate stimulus to the irradiation surface. When the irradiation distance is equal to or less than the above upper limit value, an effect such as cure can be further enhanced.

A temperature of the irradiation surface at a position distant from the nozzle irradiation opening 9*a* by between 1 mm or more and 10 mm or less is preferably 40° C. or less. When the irradiation surface has a temperature of 40° C. or less, stimulus to the irradiation surface can be reduced. A lower limit value of the temperature of the irradiation surface is not specifically limited, and is 10° C. or more, for example. The temperature of the irradiation surface can be adjusted by controlling an alternating voltage applied to a space between the first electrode 4 and the second electrode 5, an ejection volume of the active gas to be applied, a way from the distal end 4*d* of the first electrode 4 to the nozzle irradiation opening 9*a*, etc. in combination. The temperature of the irradiation surface can be measured by using a thermocouple.

Active species (radical, etc.) contained in the active gas may include, for example, hydroxyl radical, singlet oxygen, ozone, hydrogen peroxide, superoxide anion radical, nitrogen monoxide, nitrogen dioxide, peroxynitrite, nitrous peroxide, dinitrogen trioxide, etc. A type of active species contained in the active gas can further adjusted according to a type of the plasma generation gas.

A hydroxyl radical density (radical density) in the active gas in the active gas is preferably between 0.1 μmol/L and 300 μmol/L. When the radical density is equal to or more than the lower limit value, purification, activation, or cure of the irradiation target selected from cells, living tissues and biological individuals, can be further promoted. When the radical density is equal to or less than the upper limit value, stimulus to the irradiation surface can be reduced.

The radical density can be measured by the following method, for example. 0.2 mL of DMPO (5,5-dimethyl-1-pyrroline-N-oxide) 0.2 mol/L solution is irradiated with the active gas for 30 seconds. At this time, a distance from the nozzle irradiation opening 9*a* to a liquid level is 5.0 mm. A hydroxyl radical concentration of the solution irradiated with the active gas is measured using an electron spin resonance (ESR) method. The obtained value is the radial density.

A singlet oxygen density in the active gas is preferably between 0.1 μmol/L and 300 μmol/L. When the singlet oxygen density is equal to or more than the lower limit value, purification, activation and cure of the irradiation target such as cells, living tissues, biological individuals, etc. can be easily promoted. When the singlet oxygen is equal to or less than the upper limit value, stimulus to the irradiation surface can be reduced.

The singlet oxygen density can be measured by the following method, for example. 0.4 mL of TPC (2,2,5,5-tetramethyl-3-pyrroline-3-carboxamide) 0.1 mol/L solution is irradiated with the active gas for 30 seconds. At this time, a distance from the nozzle irradiation opening 9*a* to a liquid level is 5.0 mm. A singlet oxygen concentration of the solution irradiated with the active gas is measured using an electron spin resonance (ESR) method. The obtained value is the singlet oxygen density.

A flowrate of the active gas applied from the nozzle irradiation opening 9*a* is preferably between 1 L/min and 10 L/min. When the flowrate of the active gas applied from the nozzle irradiation opening 9*a* is equal to or more than the lower limit value, an effect of the active gas acting on the irradiation surface can be sufficiently increased. When the flowrate of the active gas applied from the nozzle irradiation opening 9*a* is less than the upper limit value, a temperature of the irradiation surface irradiated with the active gas can be prevented from excessively increasing. In addition, when the irradiation surface is wet, rapid dry of the irradiation surface can be prevented. Further, when the irradiation surface is an affected area, stimulus to a patient can be suppressed. In the active gas irradiation apparatus 100, a flowrate of the active gas applied from the nozzle irradiation opening 9*a* can be adjusted by a volume of the plasma generation gas supplied to the tubular dielectric 3.

The active gas generated by the active gas irradiation apparatus 100 has an effect of promoting cure of traumatic injuries and abnormalities. By applying the active gas to cells, living tissues, or biological individuals, purification and/or activation of the irradiated portion, or cure of the irradiated portion can be promoted.

When the active gas is applied in order to promote cure of traumatic injuries and/or abnormalities, there is no particular limitation on a frequency of irradiation, a number of times of irradiation, and a period of irradiation. For example, when an affected area is irradiated with the active gas with an irradiation volume between 1 L/min and 5.0 L/min, irradiation conditions of once to five times a day, for 10 seconds to 10 minutes each time, over a day to 30 days, etc. are preferred from the viewpoint of promoting cure.

The active gas irradiation apparatus 100 in this embodiment is particularly useful as an intraoral treatment tool and dental treatment tool. In addition, the active gas irradiation apparatus 100 in this embodiment is suitable as an animal treatment tool.

In the above, one embodiment has been described with reference to the specific example, but the above specific example does not intend to limit the embodiment. The aforementioned one embodiment can be carried out in various other specific examples, and can be variously omitted, replaced and modified without departing from its scope.

Modification examples are described herebelow with reference to the drawings. In the below description and the drawings used for the below description, the same reference numerals as those used for the corresponding parts in the specific example described above are used for parts that can be configured in the same way as in the specific examples described above, and redundant description is omitted.

First Modification Example

Figure 9:
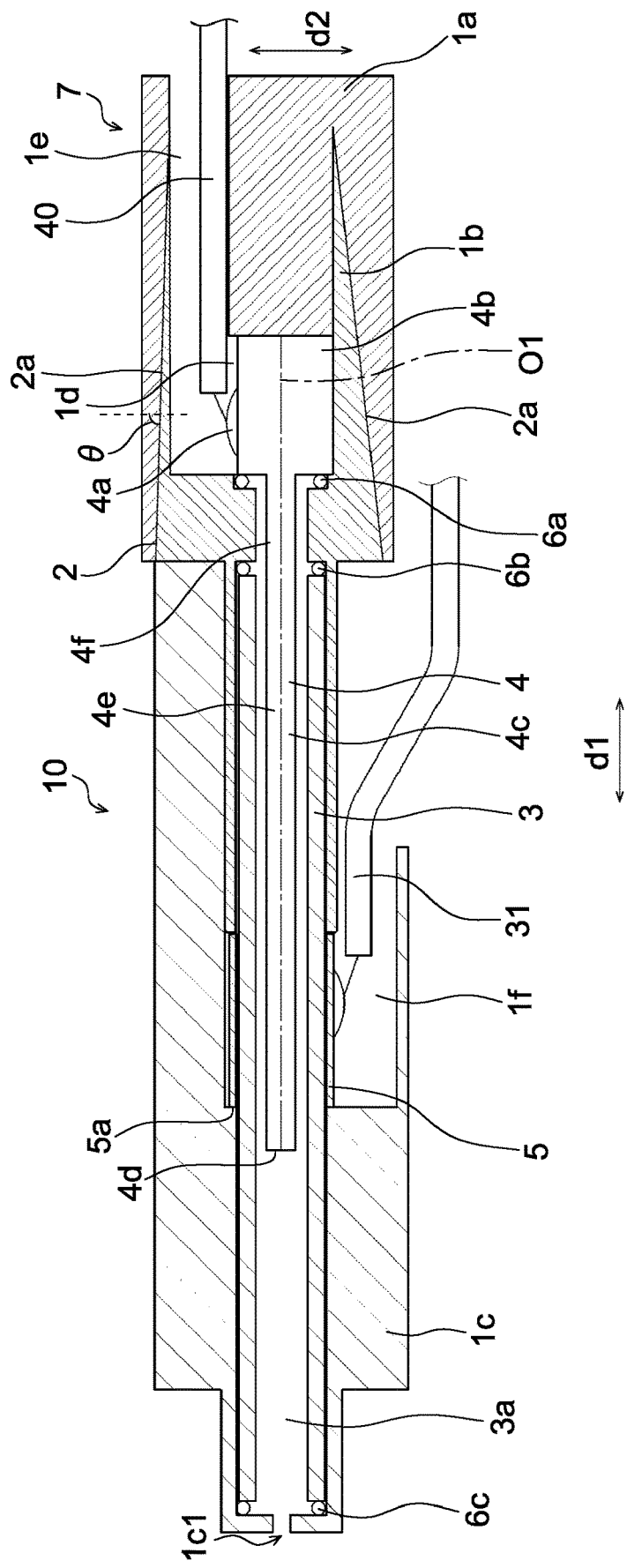
FIG. 9 is a sectional view of the irradiator according to a first modification example.

In the aforementioned embodiment, the example in which the non-perpendicular contact surface 2a defines an angle of 90° with respect to the radial direction d2 is described. However, the angle θ defined by the non-perpendicular contact surface 2a with respect to the radial direction d2 is not limited thereto. FIG. 9 is a sectional view showing an irradiator 10 according to a first modification example. In the example shown in FIG. 9, the angle θ is not 90°. In addition, the contact surface 2 does not include the perpendicular contact surface 2b. The non-perpendicular contact surface 2b preferably defines an angle θ that is larger than 45° with respect to the radial direction d2. This case can elongate the creeping distance between the first electrode 4 and an object outside the holding member 1, as compared with a case in which the angle θ is 45° or less.

Second Modification Example

Figure 10:
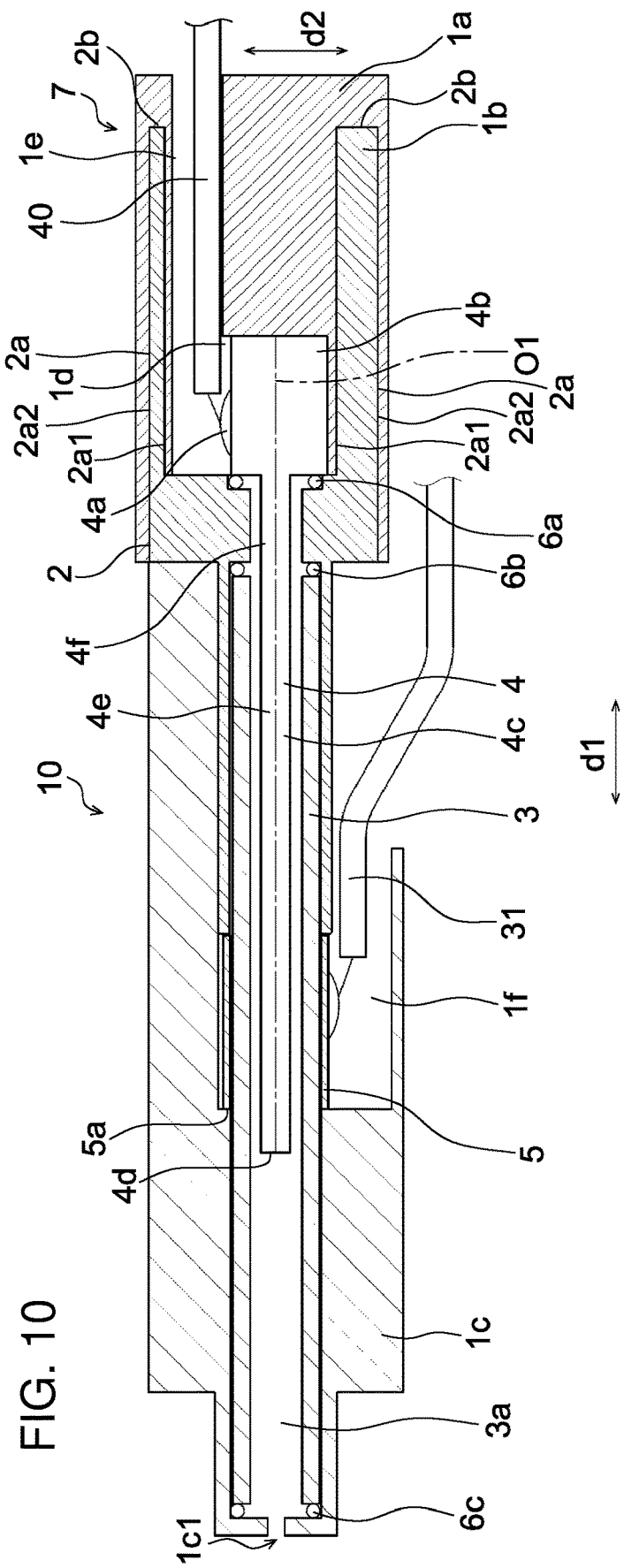
FIG. 10 is a sectional view of the irradiator according to a second modification example.

FIG. 10 is a sectional view showing the irradiator 10 according to a second modification example. In the example shown in FIG. 10, the non-perpendicular contact surface 2a includes a first non-perpendicular contact surface 2a1, and a second non-perpendicular contact surface 2a2 apart from the first non-perpendicular contact surface 2a1 in the radial direction d2. In this modification example, the first non-perpendicular contact surface 2a1 and the second non-perpendicular contact surface 2a2 respectively surround the first electrode 4 from circumferences about the axis O1. Since the non-perpendicular contact surface 2a includes the first non-perpendicular contact surface 2a1 and the second non-perpendicular contact surface 2a2, the creeping distance between the first electrode 4 and an object outside the holding member 1 can be made longer.

Third Modification Example

Figure 11:
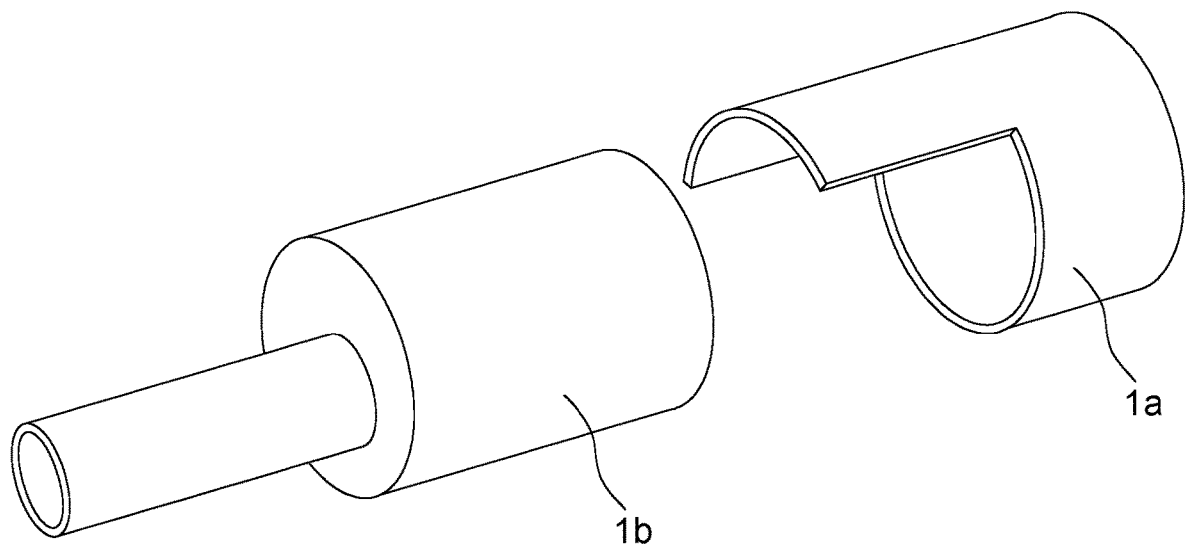
FIG. 11 is a perspective view of the first member and the second member of the holding member according to a third modification example.
Figure 12:
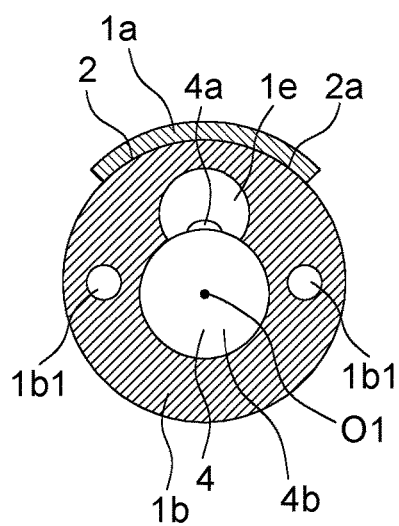
FIG. 12 is a sectional view of the irradiator according to the third modification example.

In the aforementioned embodiment and the respective modification examples, the example in which the non-perpendicular contact surface 2a surrounds the first electrode 4 from a circumference about the axis O1 is described. However, the embodiment of the non-perpendicular contact surface 2a is not limited thereto. FIG. 11 is a perspective view of the first member 1a and the second member 1b according to a third modification example. FIG. 12 is a sectional view of the irradiator 10 according to the third modification example in a plane perpendicular to the axis O1 through the terminal 4a.

In the holding member 1 in the example shown in FIGS. 11 and 12, when the first member 1a and the second member 1b are brought into contact with each other, the non-perpendicular contact surface 2a is formed partially in the circumferential direction about the axis O1. In the example shown in FIG. 12, the non-perpendicular contact surface 2a is located outside the terminal 4a in the radial direction d2. In this case, the non-perpendicular contact surface 2a can effectively suppress a short circuit between the terminal 4a and an object outside the holding member 1.

Fourth Modification Example

In the aforementioned embodiment and the respective modification examples, the example in which the first member 1a and the second member 1b have a substantially cylindrical shape, and the accommodation space 1d is formed by bringing the first member 1a and the second member 1b to align the first member 1a and the second member 1b in the axial direction d1 is described. However, the embodiment of the first member 1a and the second member 1b is not limited thereto, as long as they come into contact with each other to form the accommodation space 1d and the contact surface 2 including the non-perpendicular contact surface 2a. For example, the first member 1a and the second member 1b both have a semi-cylindrical shape. In this case, a cylindrical shape can be formed by bringing the first member 1a and the second member 1b to each other, and an inside of the cylindrical shape can serve as the accommodation space 1d.

Fifth Modification Example

In the aforementioned embodiment and the respective modification examples, the example in which the second electrode 5 is electrically grounded is described. However, the embodiment of the second electrode 5 is not limited thereto, and a voltage may be applied to the second electrode 5. For example, an alternating current displaced by half a cycle is applied to the first electrode 4 and the second electrode 5. In this case, the aforementioned positional relationship between the first electrode 4 and the contact surface 2 may be applied to a positional relationship between the second electrode 5 and the contact surface 2.

The aspect of the present invention is not limited to the aforementioned respective embodiments, and includes various modifications conceivable to those skilled in the art. The effect of the present invention is also not limited to the aforementioned contents. Namely, various additions, modifications and partial deletions are possible without departing from the conceptual idea and purpose of the invention derived from the content defined in the claims and their equivalents.

The invention claimed is:

1. An irradiator comprising:
   a first electrode to which a voltage is applied for generating a plasma; and
   a holding member holding the first electrode;
   wherein:
   the holding member has a first member and a second member that are in contact with each other to constitute an accommodation space accommodating the first electrode;
   a contact surface between the first member and the second member includes a non-perpendicular contact surface that is non-perpendicular to an axis of the first electrode; and the non-perpendicular contact surface includes a first non-perpendicular contact surface, and a second non-perpendicular contact surface that is apart from the first non-perpendicular contact surface in a radial direction perpendicular to the axis.

2. The irradiator according to claim 1, wherein any perpendiculars toward the axis through the non-perpendicular contact surface is non-parallel to the non-perpendicular contact surface.

3. The irradiator according to claim 1, wherein the non-perpendicular contact surface defines an angle that is larger than 45° with respect to a radial direction perpendicular to the axis.

4. The irradiator according to claim 1, wherein the non-perpendicular contact surface surrounds the first electrode from a circumference about the axis.

5. The irradiator according to claim 1, wherein:
the first electrode has a terminal connected to an external power source; and
the non-perpendicular contact surface is located outside the terminal in a radial direction perpendicular to the axis.

6. The irradiator according to claim 5, wherein:
the contact surface includes a perpendicular contact surface perpendicular to the axis; and
the perpendicular contact surface is located in an area different from an area in which the terminal is located in a direction along which the axis extends.

7. An irradiator comprising:
a first electrode to which a voltage is applied for generating a plasma; and
a holding member holding the first electrode;
wherein:
the holding member has a first member and a second member that are in contact with each other to constitute an accommodation space accommodating the first electrode;
a contact surface between the first member and the second member includes a non-perpendicular contact surface that is non-perpendicular to an axis of the first electrode;
the first electrode has a larger diameter part having a largest outward projection length in a radial direction perpendicular to the axis; and
the non-perpendicular contact surface is located outside the larger diameter part in the radial direction.

8. The irradiator according to claim 7, wherein:
the contact surface includes a perpendicular contact surface perpendicular to the axis; and
the perpendicular contact surface is located in an area different from an area in which the larger diameter part is located in a direction along which the axis extends.

9. The irradiator according to claim 1, wherein:
a second electrode is attached to the holding member such that the second electrode is opposed to a part of the first electrode; and
the non-perpendicular contact surface is located in an area different from an area in which the second electrode is located in a direction along which the axis extends.

10. The irradiator according to claim 1, comprising an outer cylinder member that is electrically grounded and accommodates the first electrode entirely, wherein the non-perpendicular contact surface is located between the first electrode and the outer cylinder member.

11. A plasma apparatus comprising the irradiator according to claim 1.

* * * * *